United States Patent
Andrews et al.

(10) Patent No.: US 6,889,551 B2
(45) Date of Patent: May 10, 2005

(54) METHOD OF ESTIMATING TIMBER STIFFNESS PROFILES

(75) Inventors: Michael Kenneth Andrews, Wellington (NZ); Christopher Anthony Gerard Desmond, Thames (NZ)

(73) Assignee: Carter Holt Harvey Limited, Auckland (NZ)

( * ) Notice: Subject to any disclaimer, the term of this patent is extended or adjusted under 35 U.S.C. 154(b) by 0 days.

(21) Appl. No.: 10/257,466

(22) PCT Filed: Apr. 12, 2001

(86) PCT No.: PCT/NZ01/00064

§ 371 (c)(1),
(2), (4) Date: Feb. 3, 2003

(87) PCT Pub. No.: WO01/77669

PCT Pub. Date: Oct. 18, 2001

(65) Prior Publication Data

US 2003/0150277 A1 Aug. 14, 2003

(30) Foreign Application Priority Data

Apr. 12, 2000 (NZ) .............................................. 503953

(51) Int. Cl.⁷ ........................... G01N 33/46; G01N 3/30
(52) U.S. Cl. .............................. 73/597; 73/602; 700/35; 700/84
(58) Field of Search ......................... 73/597, 601–602, 73/624, 627–628, 73, 75, 159, 160, 432.1, 801; 702/35, 38–40, 81, 179–181, 84

(56) References Cited

U.S. PATENT DOCUMENTS

| 4,879,752 A | * | 11/1989 | Aune et al. .................. 382/141 |
| 4,926,691 A | | 5/1990 | Franklin et al. .............. 73/579 |
| 4,941,357 A | * | 7/1990 | Schajer ........................ 73/600 |
| 6,272,437 B1 | * | 8/2001 | Woods et al. ................. 702/35 |

FOREIGN PATENT DOCUMENTS

| DE | 4435975 | * | 4/1995 | ............. B07C/5/34 |
| EP | 0261487 | | 3/1988 | |
| EP | 0403020 | | 12/1990 | |
| GB | 1244699 | * | 9/1971 | .......... G01N/29/04 |
| JP | 060018388 | * | 1/1994 | ............ G01N/3/30 |
| JP | 07103945 | | 4/1995 | |
| WO | WO 88 10415 | | 12/1988 | |
| WO | WO9427138 | * | 11/1994 | ......... G01N/23/203 |
| WO | WO 98 01737 | | 1/1998 | |
| WO | WO 99 44059 | | 9/1999 | |
| WO | WO 00 36413 | | 6/2000 | |

* cited by examiner

Primary Examiner—Hezron Williams
Assistant Examiner—Rose M. Miller
(74) Attorney, Agent, or Firm—Dann, Dorfman, Herrell and Skillman, P.C.

(57) ABSTRACT

The invention relates to methods and apparatus for estimating stiffness or elasticity profiles across timber. This involves measuring a velocity of a plane compression wave propagating in the timber, determining density information relating to the timber and estimating an initial elasticity profile. A reiterative process is then conducted whereby a revised elasticity profile is determined using the density information and initial elasticity profile. The revised elasticity profile is then used to determine how the timber is utilised.

35 Claims, 9 Drawing Sheets

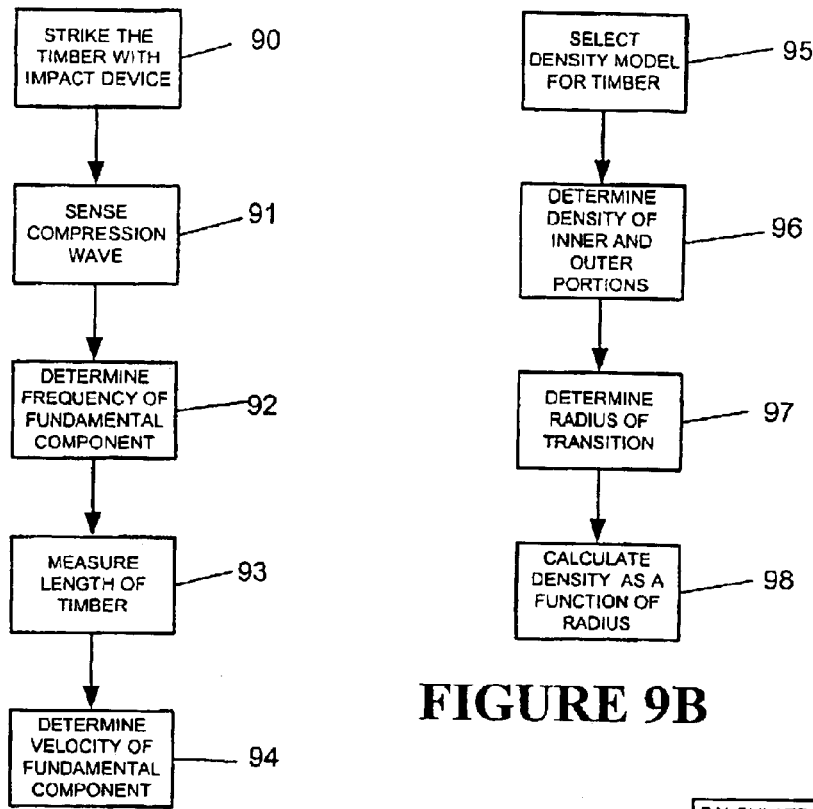
FIGURE 9A
FIGURE 9B
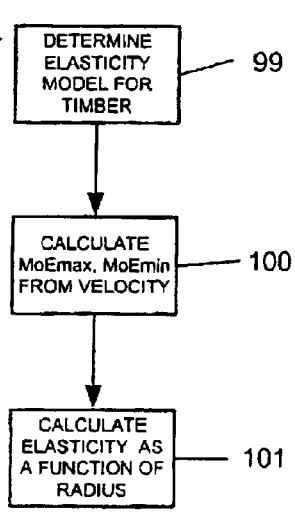
FIGURE 9C
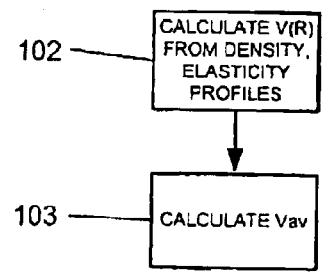
FIGURE 9D

METHOD OF ESTIMATING TIMBER STIFFNESS PROFILES

FIELD OF THE INVENTION

The present invention relates to a method and apparatus for estimating timber stiffness profiles with a view to extracting the best value from a log.

BACKGROUND TO THE INVENTION

Generally where all or part of a log is not destined to be pulped it is usual to categorise the lumber to be taken by a log break down system into that which is destined to be cut to structural dimensions and that which is to be cut to industrial dimensions. Wood which is sufficient stiffness for structural application is usually broken down into timbers for construction or similar applications.

Stiffness is a lesser concern for generating industrial applications and industrial dimensioned lumber issued in a variety of end uses such as the making of packing cases for example.

The outer wood or sap wood from a log or tree stem is generally of higher stiffness than the core of the log or stem, or heart wood. In general structual application lumber has the highest market value and it is desirable to saw tree stems or logs so as to maximise the value of wood which is cut to structural dimensions. There can be a significant pricing differential per unit value between structural dimensioned lumber and industrial dimensioned lumber. By way of example to a specific instance, we wish to refer to two types of mistake that might be made in a break down system.

New Zealand patent specification 333434 discloses a procedure which enables in the forest (at a skid site) a reasonable determination of the average stiffness of a tree stem and thus logs to be cut therefrom. New Zealand patent specification 331527 discloses a related method appropriate for determining those tree stems and/or logs that are suitable for pulping.

PCT international patent application US98/23921 published as WO 99/44059 discloses a method of lumber break down to maximise the value of the lumber recovered from a log by a system which includes measuring the length of the log and determining a stress wave velocity in the log, to predict an average modulus of elasticity. It is clear that an average velocity for the full log section or tree stem section is utilised.

SUMMARY OF THE INVENTION

The present invention wishes to maximise value to be derived from a log on the basis of an understanding that educated guesses as to conservative parallel cuts of a section of a log can be made of a log likely to have some structural stiffness with the half rounds or wings having little, if any, wood therein of an industrial only wood quality. Such an approach leaves a cant capable of being more accurately pretested prior to breakdown. Where desired wings or round backs cut from a particular tree stem or log back can be indexed to their cant.

In one aspect the present invention may be said to consist in a method of breaking down a stem, log, cant or slab which comprises or includes the steps of: determining an acoustic velocity value for the stem, log, cant or slab, predicting a stiffness profile across the stem, log, or cant as a function of the acoustic velocity and a density profile across the stem, log, cant or slab, and utilising the stiffness profile in cutting the stem, log, cant or slab.

In another aspect the present invention may be said to consist in a method of estimating elasticity or stiffness across a length of timber including: measuring the velocity of a compression wave in the timber, providing information as to density for the timber, calculating an initial profile of elasticity or stiffness across the timber using an elasticity model of the timber, and determining a revised elasticity or stiffness profile using the measured velocity, density information and initial elasticity profile.

In another aspect the present invention may be said to consist in method of estimating elasticity or stiffness across a length of timber including: measuring the velocity of a compression wave in the timber, providing information as to density for the timber, calculating a profile of elasticity or stiffness across the timber using an elasticity model of the timber, and validating the elasticity or stiffness profile by calulating a velocity of a compression wave in the timber using the density information and elasticity or stiffness profile and comparing the calculated velocity with the measured velocity.

In another aspect the present invention may be said to consist in apparatus for breaking down a tree stem, log, cant or slab of wood including: means arranged to determine an acoustic velocity value for the stem, log, cant or slab, means arranged to predict a stiffness profile across the stem, log, cant or slab as a function of the acoustic velocity and a density profile across the stem, log, cant or slab.

In another aspect the present invention may be said to consist in apparatus for estimating elasticity or stiffness across a length of timber including: means for measuring the velocity of a compression wave in the timber, means for providing information as to density for the timber, and means arranged to calculate an initial profile of elasticity or stiffness across the timber using an elasticity model of the timber, and to determine a revised elasticity or stiffness profile using the measured velocity, density information and initial elasticity profile.

In another aspect the present invention may be said to consist in apparatus for estimating elasticity or stiffness across a length of timber including: means for measuring the velocity of a compression wave in the timber, means for providing information as to density for the timber, and means arranged to calculate a profile of elasticity or stiffness across the timber using an elasticity model of the timber, and to validate the elasticity or stiffness profile by calulating a velocity of a compression wave in the timber using the density information and elasticity or stiffness profile and comparing the calculated velocity with the measured velocity.

In another aspect the present invention may be said to consist in a method of managing the breakdown of a tree stem which comprises or includes the steps of: felling the tree stem, assessing the tree stem for breakdown into sawn timber, optionally cutting the tree stem into a log or logs, breaking tree stem or log(s) down into a cant and side parts, cutting the side parts to structural timber pieces, cutting the cant to a mixture of timber pieces cut to structural dimensions and to industrial dimensions, the cutting pattern of the cant having been determined with reliance upon the product of the average density or a density profile across the cant and a function of an average acoustic speed of the tree stem, cant or log.

In another aspect the present invention consists in a variation of the method previously defined where a density indicative of an average density of the stem, log, cant or slab is instead utilised rather than a density profile across the cant. Thereafter the determination of an appropriate cutting pattern is related to both the square of the acoustic speed of the cant and that density.

BRIEF DESCRIPTION OF THE DRAWINGS

The invention is now described with reference to the accompanying drawings in which:

FIGS. 9A–9D show in further detail a preferred form method for estimating an MoE profile, and FIG. 10 schematically illustrates one form of apparatus of the invention for estimating an MoE profiles for logs or cants.

DETAILED DESCRIPTION OF PREFERRED EMBODIMENTS

In the method of the invention an acoustic or sonic velocity measure obtained for a log or cant is combined with a radial density profile for the log or cant which will typically be green, i.e. undried and typically freshly cut and thus high moisture content, to derive a radial profile of its MoE, not just a single value. This MoE stiffness profile can be used to estimate the dry MoE of timber sawn from the sample and to determine how to saw the log or cant to maximise recovery of high value timber for structural applications.

The method of the invention has been found particularly suitable for species like *pinus radiata* which typically exhibit a clear heartwood-sapwood transition in stems logs or cants. The respective densities of the heartwood and sapwood is dominated by water content and the heart-sap transition provides an adequate starting point for a density profile. It is believed that the method of the invention will also be sutiable for use with stems, logs or cants of other species also.

When a wood stem or log or cant receives an acoustic impulse, typically generated by striking the sample, with a hammer for example, the speed of longitudinal waves can be calculated from the formula $$V = 2f_0 L \qquad \qquad 1$$

where L is the sample length, $f_0$ the fundamental or lowest longitudinal mode, and V the desired speed of longitudinal compression (i.e. sound) waves. V is in turn related to the modulus of elasticity E, or MoE, by the expression $$V^2 = E/\rho \qquad \qquad 2$$

where $\rho$ is the material density of the wood. Thus for velocity and in particular from $f_0$, it is possible to determine an MoE value or value indicative of MoE for the sample. Any suitable system for measuring acoustic velocity may be used.

Figure 1:
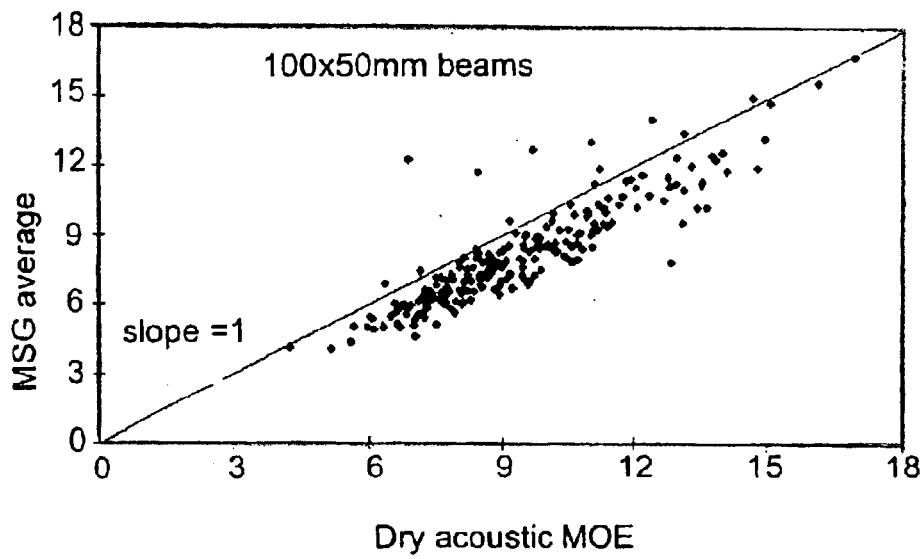
FIG. 1 is a plot of machine stress grade (MSG) MoE values in GPa for many 100×50 mm beams against their dry MoE values assessed using an acoustic velocity technique.

In equation 2, it is important to realise that the relevant density is simply the mass to volume ratio, including the mass of water. We have demonstrated (see Andrews M K and Harris P D, p31, Sensors and Their Applications, eds White N M and Augousti A T, IOP press 1999) that when density is so defined, the acoustic-measured MoE remains constant as timber dries from green until the Fibre Saturation Point is reached; in further drying to equilibrium moisture content (about 12% in New Zealand) the sonic modulus increases by perhaps 20%. This behaviour replicates stiffness results found by conventional bending measurements. Further, experiments show that the bending modulus measured over many samples approaches but does not exceed the acoustic value. Typically, the bending value may be up to 20% lower than the acoustic value. Some of this difference will be due to point defects such as knots which degrade the bending value but have little effect on the acoustic measurement. The significant point is that when density includes water content, the sonic modulus and the bending modulus measure the same quantity. FIG. 1 illustrates the agreement between the sonic modulus and the along-beam average of the machine stress grade measured MoE for a number of 100×50 mm beams.

Finite element modeling, backed by measurements on boards cut from green logs, show that the speed measured in sonic techniques is very close to the area-weighted average speed over the sample cross section. However it is well known that in wood such as *p. radiata*, the MoE increases radially from the pith to the outer wood. Measurements reveal that this increase is approximately parabolic in *p. radiata* and typically increases from 6 GPa in the core to 12 GPa at the bark. The heartwood density, including water, is typically about 500 kg/m³, with an abrupt change to about 1050 kg/m³ in the sapwood. Other species will have their particular characteristics since the acoustic velocity is governed by the MoE/density ratio, the speed at the core equals that near the bark. However there is an acoustic velocity peak at the sapwood boundary and beyond this boundary, is the sapwood itself acoustic velocity drops abruptly in response to the density rise. In general in *p. radiata*, the effect of the radial density variations is to partially smooth out radial variations in longitudinal acoustic velocity.

The table below shows the results of a calculation which splits a typical log, 6 m long and 350 mm is diameter, into three concentric regions approximating the densities and moduli of pine:

TABLE

|  | region 1 0–75 mm | region 2 75–125 mm | region 3 125–175 mm | region 3 log | Composite log | area weighted means |
|---|---|---|---|---|---|---|
| Wet density | 550 | 800 | 1050 |  |  |  |
| Wet MoE | $6 \times 10^9$ | $7.510^9$ | $9.210^9$ |  |  |  |
| speed, km/s | 3.30 | 3.06 | 2.96 | 2.94 | 3.01 | 3.06 |

The acoustic velocity in the three regions, beginning with the core at a radius between 0 and 75 mm, are calculated from equation 9. In column 5, the acoustic velocity in a log consisting entirely of the material of region three was found by Finite Element (FE) calculation using full elastic theory to be 2.94 km/s, which the table shows is. 0.7% below the velocity expected from equation 2. The composite three-region log was calculated by FE to have an acoustic velocity of 3.01 km/s. The final column gives the area-weighted average of the simply-calculated acoustic velocity in the three regions. The FE composite value is 1.7% lower than this. If it is allowed that FE calculations return answers 0.7% lower than the simple estimates which do not include full elastic behaviour, then the composite velocity is within 1% of the area-weighted one. This is less than experimental error encountered in actual measurements. In an extreme and non-physical log model in which MoE increased by four and velocity by almost three across a diameter, the area weighted velocity was only 11% away from the full FE solution for the velocity. In actual logs, the area weighted speed is expected to be a good estimate of the true acoustic velocity. In experiments where cants have been sawn into a number of beams of equal size, it has been found that the beam average equals the speed of the cant, which is consistent with the FE results, since each beam should contribute equally to the average. In particular when 50 cants each 100 mm thick were sawn into typically five 100×50 mm pieces of timber the ratio of the average speed of a wave in the pieces to the velocity of a wave in the cant lay between 0.97 and 1.03; the average value of this ratio for the 50 cants was 1.003.

In general terms, the approach of one preferred form of the invention is to use information known from log samples to construct radial profiles of typical MoE/stiffness and density. These imply a radial variation in longitudinal acoustic velocity. This acoustic velocity profile weighted (for example by radius for logs, or equally weighted for a cants, is integrated across the log or cant and is compared with the sonic measurement. If the answers differ the MoE/stiffness profile is modified.

Figure 2:
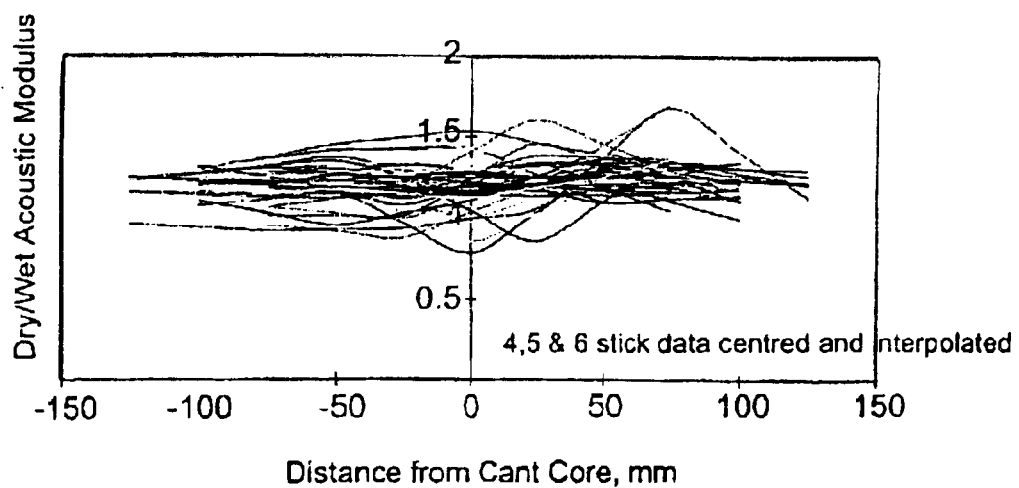
FIG. 2 is a plot of dry/wet acoustic modulus against distance from cant core in mm for a number of cants.

The preferred procedure is intended for use with green or undried wood, first because sawing decisions clearly relate to green timber, and second because the water content at this stage largely determines the density. It does this overwhelmingly in the sapwood, and partially in the drier heartwood. A dry MoE can be estimated from a wet value by simply increasing the values by about 20%. This is demonstrated in FIG. 2, which ratios the dry and wet acoustic MoE of a number of 100×50 mm beams cut from p. radiata cants of different size. Whether heartwood or sapwood, which have quite different water content, large-size cants (producing more beams) or small, the ratio remains close to 1.2.

The method is based on knowledge of the population, and must therefore be adapted for local species or growing conditions. It has been found for example, the speed in a wet cant or log gives a robust (within 10%) indication of the stiffness of the wood some 50 mm in from the bark, but a less reliable indication of the core wood stiffness. Between the two, the stiffness of most logs follows a roughly parabolic law. These two regressions allow a parabolic test MoE profile to be generated. The simplest wet density profile can be estimated from a measurement of the heartwood-sapwood transition.

In preferred forms of the invention the raidal velocity profile implied by the MoE and density is integrated across the sample, and the MoE profile is first shifted up or down, by a maximum of 10% for example, to seek agreement with the measured log or cant velocity. If agreement is not reached within this range, the outer MoE is then clamped, and the core MoE value raised or lowered to generate agreement. (The outer MoE has been found to be more tightly defined by log or cant speed than the core MoE.)

The method relies on some prior knowledge of the kind of stiffness profile to be expected. In most trees the inner or juvenile wood is weaker than the older wood near the bark so in general stiffness will be expected to increase radially outwards. In the experiments referred to earlier 50 logs where cut into cants and then into 100×50 mm sticks typically 5 m in length. The sticks were dried and machine stress graded to enable a model of the elastic MoE of p. radiata sawlogs to be derived from pith to bark. The MoE of each stick was found by measuring the velocity of a plane compression wave in each stick, weighing each stick to calculate its wet density, and then calculating the stick MoE using equation 2. Inspection of all the data showed that at the resolution afforded by the 500 mm stick widths the radial profile of MoE in each cant was approximately parabolic rising perhaps by 5 Gpa from the value at the core to its value near the bark. Using such a parabola can lead to non-physical values and therefore the parabolic rise was limited to a value of 13 Gpa. Measurements at higher resolution than the trial suggested that an MoE model with a low core value and an asymptotic approach to a bark value could be used. The method of the invention is not restricted to one type of model and therefore any suitable model could be used.

Regardless of the basic dry density, the density of the outer sapwood in green p. radiata is close to 1050 kg/m$^3$, while that of the drier inner wood is more variable but typically around 550 kg/m$^3$. The result is that the acoustic velocity in this species is not a strong function of radius. The velocity in the weak inner wood is raised by its lightness while the velocity in the stronger outer wood is lowered because of its higher density. The speed at any location is found to be not far from the average velocity for the whole log or cant. The location of particular interest is the zone near the bark where it is known that all p. radiata trees have a density of about 1050 kg/m$^3$. Combining this density with the acoustic velocity for the whole log or cant gives an estimate of the MoE of the wood near the bark. The MoE information can be refined if more information on the wet density is available. The approach is to begin with a first estimate of a radial profile based on equations formulated from experimental data which indicate the likely core and bark values of MoE and a radial profile of wet density which is assumed to be correct (or may be measured for each log or sample). The density and MoE profiles define a radial profile of acoustic velocity whose appropriately weighted average should equal that measured sonically for the whole log or cant. If the computed velocity does not agree with the measured value corrections to the MoE must be made as will be described in detail below.

Variations are possible. For example, constraints can be put on the radial MoE profile to prevent non-physical results occurring, and other modifications to a parabolic profile can be incorporated. These will depend on knowledge of the particular species likely to be encountered. It is known from the literature that corewood MoE correlates with dry (and wet) density, so when core MoE is changed, a corresponding change in the density may be made. Any measurement which generates a more accurate density profile is desirable.

Figure 3A:
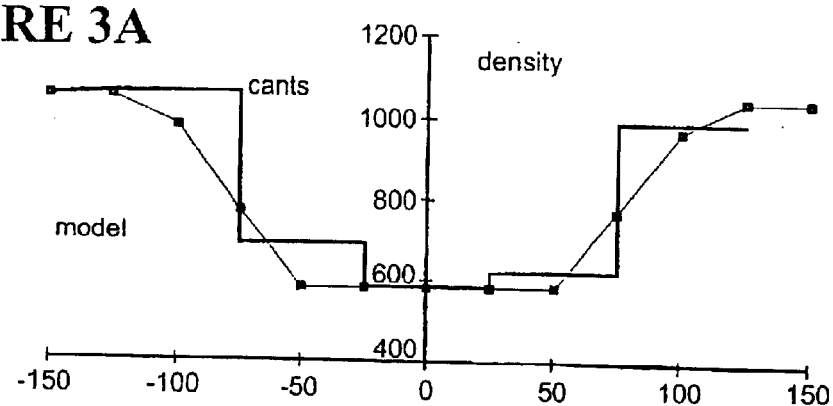
FIG. 3A is a plot of cant density against distance from the cant centre in which the heavier line is a plot through a number of measured density points for a *pinus radiata* cant and the lighter line is a plot of the density forecast by a model.
Figure 3B:
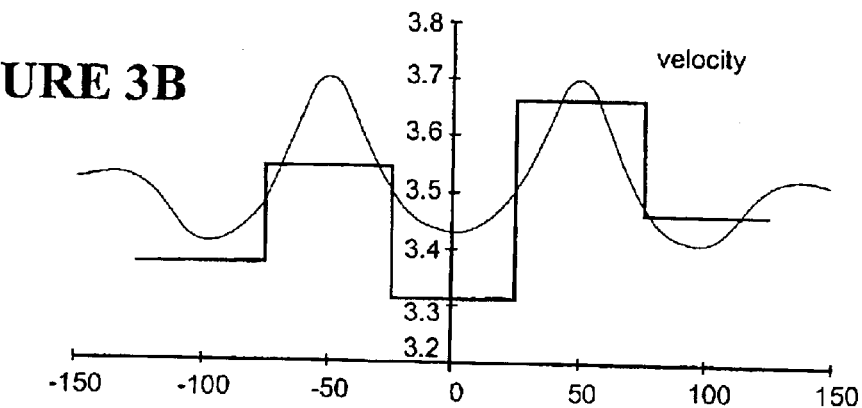
FIG. 3B is a plot of acoustic velocity against distance from cant centre for a cant in which the heavier line is a plot through a number of measured points and the lighter line is a plot forecast by a model.
Figure 3C:
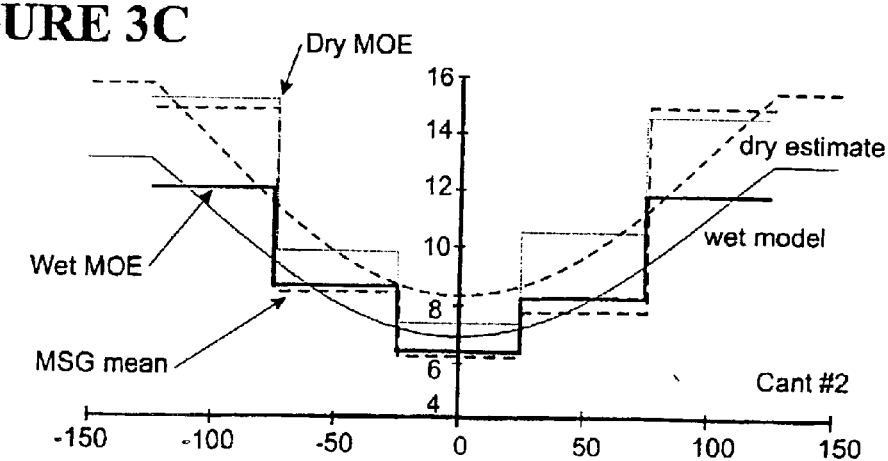
FIG. 3C shows how a combination of the square of the velocity of FIG. 3*b* when multiplied by the density of FIG. 3*a* provides a better estimate than mere acoustic speed or stiffness derived from the square of the speed for the same cant profile, FIG. 3*c* showing dry and wet MOEs.
Figure 4:
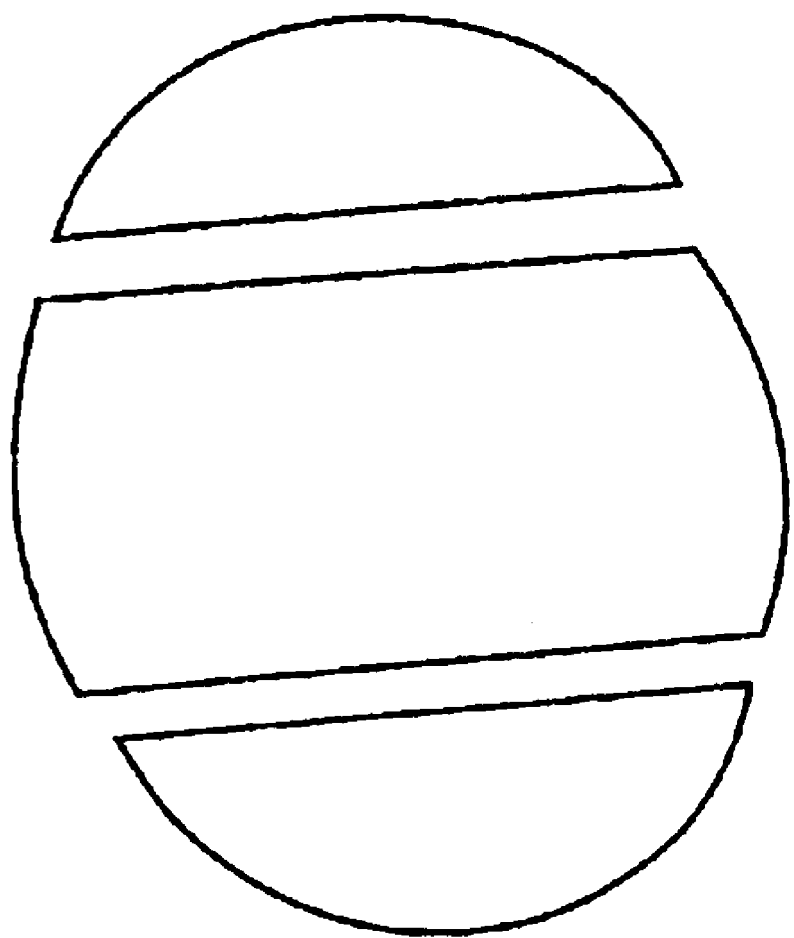
FIG. 4 shows a typical sawing pattern for a log to form two side slabs (sometimes referred to as wings) and a cant.

FIGS. 3A, 3B, and 3C illustrate a prediction of the internal properties of a cant based on a single value of its acoustic speed (3.51 km/s) and a model of its wet density. Predictions are compared with measurements on five 100× 50 beams or "sticks" subsequently taken from the cant. In FIGS. 3A–C The horizontal scale is the distance in mm from the cant centre. FIG. 3A compares the assumed density profile with a plot of the measured density values for each stick. FIG. 3C shows the quasi-parabolic stiffness model (labelled "wet model") which, when combined with the density profile, would produce the observed cant speed of 3.51 km/s. FIG. 3B shows the detailed speed profile generated. Clearly the major features of the actual speed variation across the cant are reproduced.

FIG. 3C shows that there is good agreement between the wet stick MoE values and the model curve. A best-estimate dry MoE curve is drawn, which is just the wet curve raised by a factor in this case by 20% for *p. radiata*. This allows comparison to be made with the actual dry stick values, and the mean machine stress grade measured values. The MSG values tend to lie below the dry estimate, consistent with the expectation from FIG. 1.

It can be seen that there is good agreement between the predicted and actual wet MoE values in the example which confirms the feasibility of combining wet density estimates with an acoustic velocity measurement to derive a realistic wet stiffness profile, from which a dry value can be extrapolated. The better the density estimate, the more accurate the resulting profile will be, but a simple measurement of the heartwood boundary location is a simple minimum input to for example a sawing station be used to guide cutting decisions based on a target wood stiffness, but other applications are possible.

The concept of combining density and MoE profiles may be applied generally where there is prior knowledge of the types of variation expected in density and MoE, since it is based on the observation that a sonic measure yields an area-weighted average of the radial profile of sound speed. In particular, as the acoustic velocity profile does not vary much over the diameter of timber this leads to using the measured velocity to estimate $MoE_{max}$ It therefore follows that the measured acoustic velocity in an intact piece of timber can be used in determining the elasticity profile across the timber. More particularly as it is shown that the measured velocity of a plane compression wave in the entire timber is close to the value of the velocity of a plane compression wave in a portion of the timber taken from the outer wood, and as the density of the timber in this region is known to a reasonable degree of accuracy, then it follows that the MoE in this region can also be calculated to a reasonable degree of accuracy using equation 2, approximately to within 10% of the actual value. This calculated MoE of the outer wood is therefore of suitable accuracy to be used as a reference point on which an MoE profile for the entire diameter of the timber can be based upon.

Figure 5:
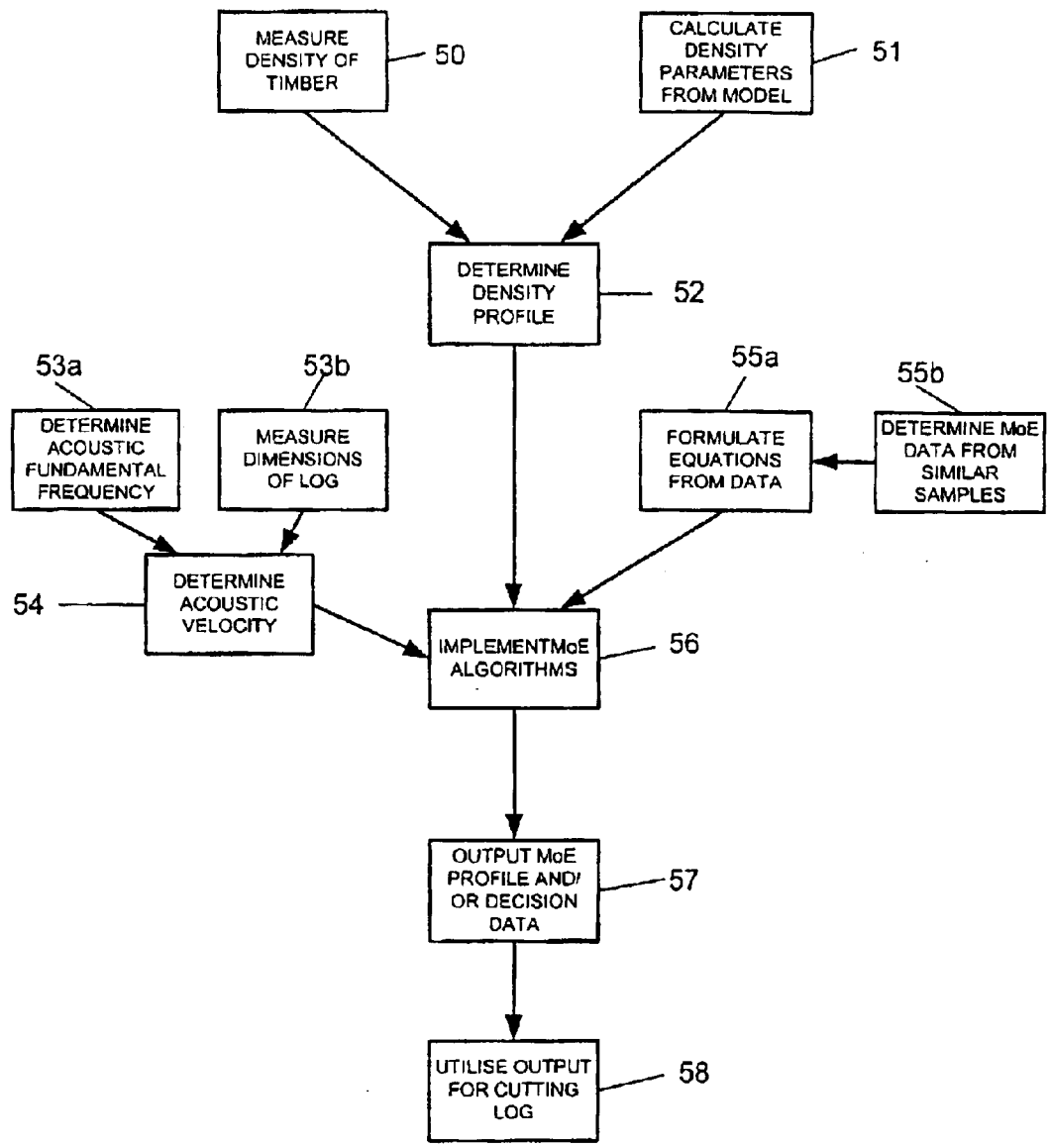
FIG. 5 is a flow diagram which comprises schematic overview of the information and processing required for MoE estimation according to the invention.

FIG. 5 is a schematic overview of the information and processing used in a preferred method of determining an elasticity profile. A density profile of the timber is determined as indicated at 52 either by using a model 51 to calculate an assumed profile, or by measuring the density profile for the stem, log or cant as indicated at 50 using a suitable technique. Then the velocity of an acoustic or other compression wave in the timber is also determined as indicated at 54. Preferably this is calculated from the plane compression wave in the timber as indicated at 53b and the length of the timber 53b. Statistical data relating to MoE characteristics of the stem, log or cant being analysed is also obtained and used to formulate characteristic MoE equations for the species as indicated at 55a and 55b. Such data will typically have been previously obtained from samples of the same species likely to have similar characteristics to the stem, log or cant to be analysed. For example the sample timber will typically have been a similar age and from a similar area, and should have been exposed to similar climatic and environmental conditions. The density, acoustic velocity, dimensional and initial MoE information obtained is then used to calculate an estimated MoE profile across the stem, log or cant as indicated at 56. The estimated MoE profile for the stem, log or cant may be output for use as indicated at 57 or alternatively used to provide information to a log breakdown sawing system or a manual saw operator, or a cut placement or a sawing pattern for the stem, log or cant to maximise the value or value as structural timber obtained. This general method can be carried out individually for each stem, log or cant that is processed.

Figure 6:
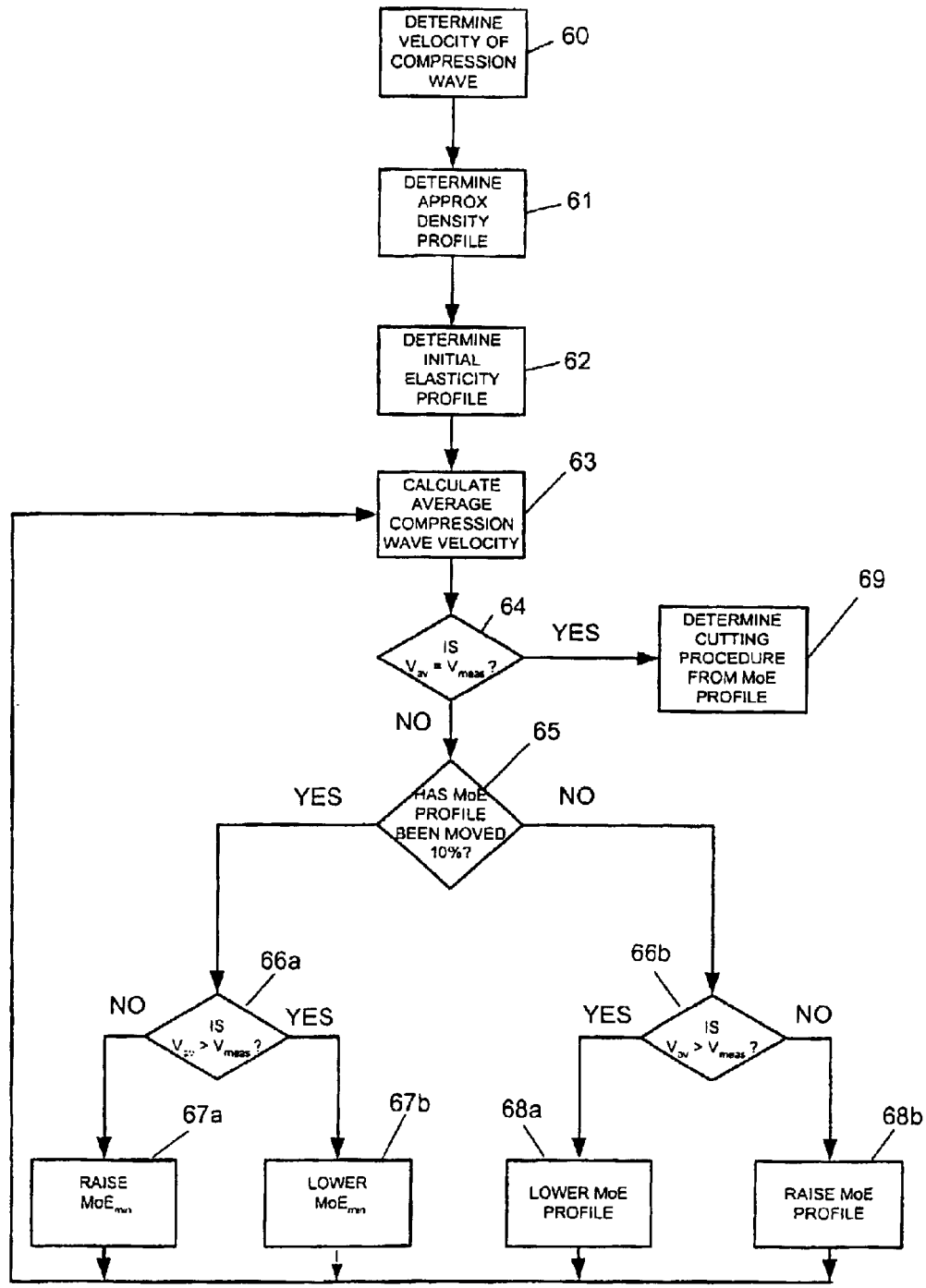
FIG. 6 is a flow diagram showing a preferred form methodology for estimating an MoE profile for a log or cant.

FIG. 6 shows a preferred method for carrying out the method shown in FIG. 5. It will be appreciated that the flow chart depicted is exemplary and many of the steps do not necessarily have to be carried out in the order shown. The actual order of implementation may be differ depending on the configuration of the apparatus carrying out the method and the requirements of the operator.

Figure 7A:
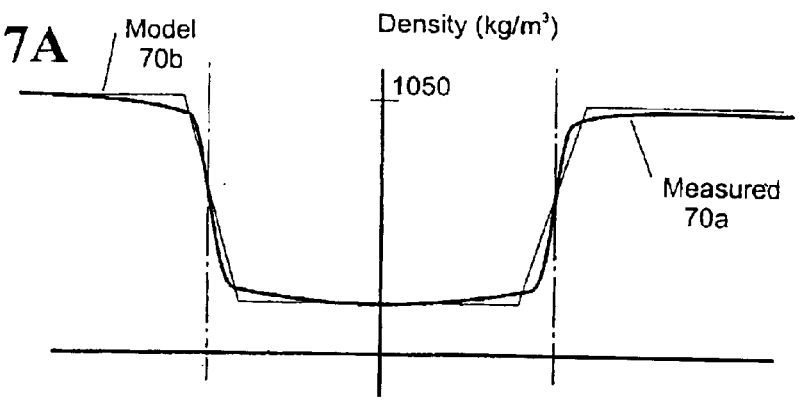
FIGS. 7A–7C show density, MoE and velocity profiles respectively as a function of timber radius.

The velocity ($V_{meas}$) of the plane compression wave in the stem, log or cant is determined as indicated at 60 using a suitable acoustic technique. A density profile across the radius of the stem, log or cant is then estimated or measured as indicated at 61 or alternatively a model density profile for the species may be used. Examples of both a measured density profile 70a and estimated density profile 70b are shown in FIG. 7A. Typically in *p. radiata* the wet density across the diameter has a low zone corresponding to the relatively dry heart or transition wood and a high zone corresponding to the water saturated sapwood. The boundary between the regions can be quite abrupt.

Figure 7B:
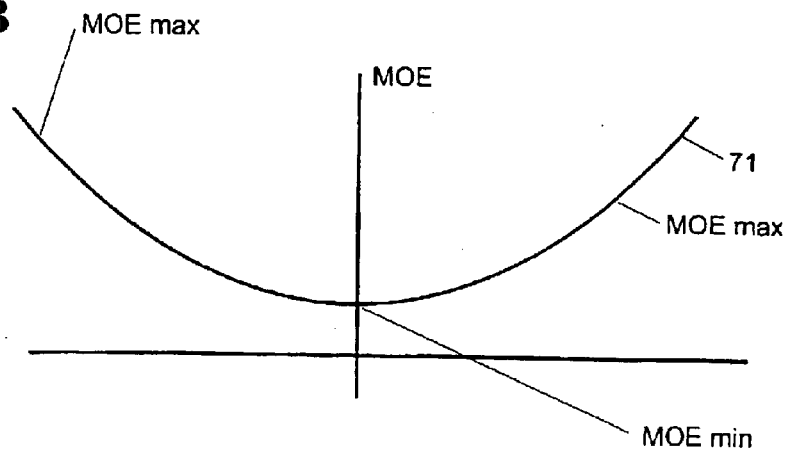
Figure 7C:
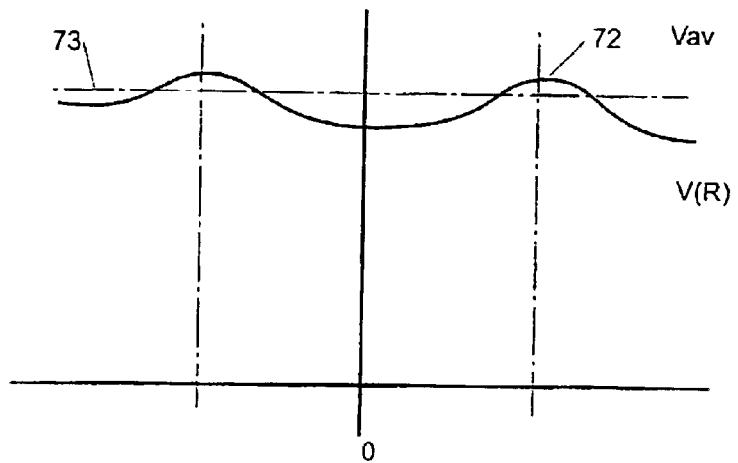

An initial MoE/elasticity profile is then determined as indicated at 62 using the measured velocity, $V_{meas}$ and an appropriate model which is formulated through experimentation. For *p. radiata* this involves determining $MoE_{max}$ corresponding to the sapwood elasticity and $MoE_{min}$ corresponding to the heartwood elasticity. An approximately parabolic curve which fits the data is then formulated which enables an initial estimate of the elasticity at all points across the diameter of the timber to be calculated. The resulting initial elasticity profile 71 (see FIG. 7B) is then utilised along with the density profile to determine a calculated velocity profile 72 across the timber (see FIG. 7C). This velocity profile indicates the predicted velocity of a plane compression wave travelling lengthwise through the timber, as a function of radius. This calculated velocity profile is then averaged as indicated at 63 in FIG. 6 to produce a value $V_{av}$. This value $V_{av}$ is also indicated in FIG. 7C by the dash-dotted line 73.

At this point an iterative process is undertaken to refine the initial estimate of the MoE/elasticity profile to determine an MoE/elasticity profile which reflects more accurately the actual elasticity across the timber. In general terms this process involves adjusting the initial elasticity profile until, using the estimated or measured density profile, the average of the calculated velocity profile $V_{av}$ more closely approximates the measured velocity of the plane compression wave in the stem, log or cant to within the desired accuracy. More particularly, $V_{av}$ and $V_{meas}$ are compared as indicated at 64 to see if the are equal or if they differ. If $V_{av} \neq V_{meas}$ then some adjustment of the initial MoE is performed. However it may not necessarily be appropriate to move the entire profile up in response to the comparision. As described previously experimentation has shown that the MoE in the outer wood or sapwood, that is $MoE_{max}$, can be calculated to within approximately 10% of the actual value. Therefore during adjustment of the MoE profile, $MoE_{max}$ is preferably not moved by more than 10% from its initial calculated value.

Figure 8A:
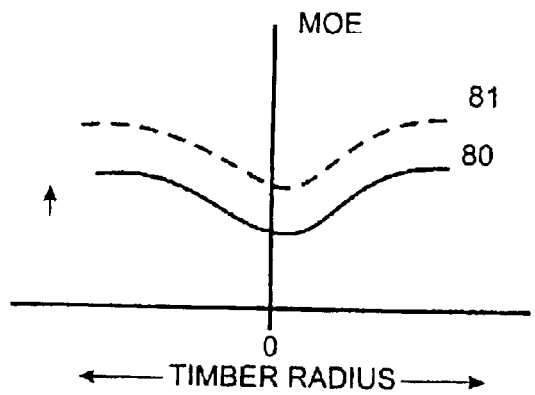
FIGS. 8A–8D show initial and revised MoE profiles as a function of timber radius.
Figure 8C:
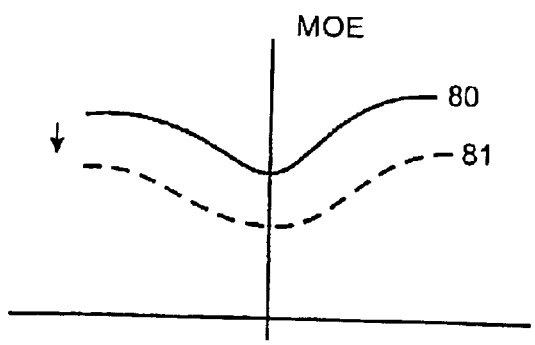

In the preferred from shown it is determined as indicated at 65 if the MoE profile has already been adjusted such that $MoE_{max}$ has been moved more than say 10%. If it has not, and this will be the case in the first iteration, then the entire MoE profile is moved upwards or downwards by a small amount. To do so it is then determined as indicated at 66b whether $V_{av} > V_{meas}$. If it is not then it is assumed that the calculated initial MoE profile is too "low" and the MoE profile is shifted upwards as indicated at 68b. FIG. 8A shows an example of an initial MoE profile 80 and a revised MoE profile 81 which has been shifted upwards. If $V_{av} < V_{meas}$ then it is assumed that the calculated MoE profile is too "high" and must be shifted downwards as indicated at 68a to produce a revised MoE profile as shown in FIG. 8C. After adjustment of the MoE profile either up or down, then $V_{av}$ is recalculated as before using the revised MoE profile and the comparison between $V_{av}$ and $V_{meas}$ is carried out again.

Figure 8B:
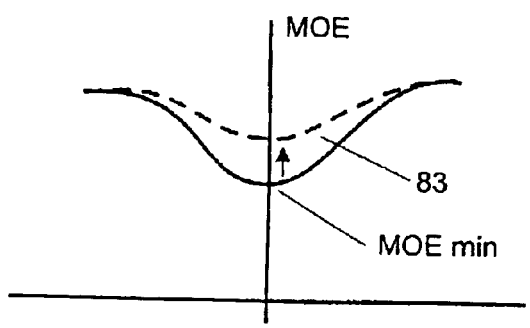
Figure 8D:
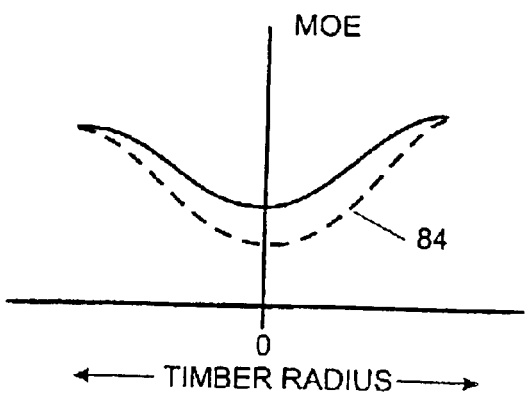

If however the comparison as indicated at 65 reveals that the MoE profile 80 has already been shifted more than 10% from the initial $MoE_{max}$ value during previous iterations, then no more movement of this value is undertaken as it is assumed the actual value should be within 10% of the initially calculated value. Therefore rather than shifting the entire MoE profile up or down, the $MoE_{min}$ value is adjusted up or down. To do so it is determined as indicated at 66a whether $V_{av} > V_{meas}$. If it is not then it is assumed that the calculated initial MoE profile is too "low". In this case the $MoE_{min}$ value is increased 67a by a small amount to produce a revised MoE profile 83 with a "flatter" shape as shown in FIG. 8B, leaving the $MoE_{max}$ value unchanged. Otherwise if $V_{av} > V_{meas}$ then it is assumed that the calculated initial MoE profile is too "high". The $MoE_{min}$ value is decreased 67b to produce a "steeper" curve 84 as shown in FIG. 5D. The revised curve 83 or 84 is then used to recalculate the average velocity as before. The comparison steps 64–66b along with the MoE profile adjustment steps 67a–68b are reiterated as appropriate until $V_{av} = V_{meas}$, at which point it is assumed that the revised MoE profile is accurate enough to be used to provide determine how the timber should be cut as indicated at 69.

Steps 60–63 shown in FIG. 6 are now be described in more detail with reference to FIGS. 9A–9D. FIG. 9A shows a preferred method of determining the velocity of a plane compression wave in the stem, log or cant which is more particularly described New Zealand patent specification 337015/337186 and New Zealand patent specification 333434 which are incorporated herein by reference.

Good accuracy in the measurement of sound speed is necessary to facilitate the present claim. New Zealand patent application 337015/337186 are considerably more accurate than the class of instrument called stress wave timers. These time a single passage of an elastic disturbance along a sample. Typically, an accuracy of 10% is achieved in deriving a speed, so that the error in the modulus E, which depends on the square of this speed, is of order 20%. Resonance tools are more accurate because they average many relections of the sound pulse (as many as 100). Repeatability of better than 1% is regularly achieved. There are also physical advantages in allowing multiple reflections to occur, because this enables a true plane wave to be developed in the sample. This cannot be guaranteed when using single pass timers on large-diameter logs, but the commonly used theory assumes that plane waves are being measured.

The length of timber is struck at one end as indicated at 90 with an impact device such as a hammer which induces a range of standing compression waves along the length of the timber. The impact device may be activated automatically using a machine or alternatively may involve manually striking the end of the timber with the hammer. A transducer is then used to detect the compression waves within the stem, log or cant as indicated at 91. The transducer can be any suitable device, such as a piezo-electric accelerometer or the like which is mounted on or near one end of the timber being examined. The output of the transducer is analysed by a processor to determine the frequency of the fundamental component $f_0$ as indicated at 92 using a suitable signal processing technique. The length of the stem, log or cant is measured as indicated at 93 and this value along with the fundamental frequency is utilised to determine the velocity of the plane wave by way of equation 1 as indicated at 94. This velocity $V_{meas}$, gives a good indication of the velocity of the plane compression wave in the sapwood as discussed previously. It will be appreciated that this is only one way of finding the compression wave velocity and other suitable techniques known to those skilled in this area of technology could be utilised.

FIG. 9B shows a preferred method of determining an estimated wet density profile 61 across the timber using a predetermined model. Firstly, the appropriate model is selected for the wood type as indicated at 95. The model, for example profile 70a as shown in FIG. 7a for p radiata, assumes a known outer sapwood density and inner heartwood density and a linear transition between the two. The density of the outer sapwood for p. radiata, is known to be close to about 1050 kg/m³ while the drier inner heartwood is more variable but typically about 550 kg/m³. Through experimentation based on the densities of wet sticks sawn from cants for p. radiata in the 50 log trial the radius in millimetres at which the wood begins to change from the drier core to the wet outer was estimated. In particular from numerical illustrations which were taken from the trial it was determined:

$$R_{core} = 0.5405D - 116 \qquad 3$$

where $R_{core}$ is the transition radius and D is the stem or log diameter. The radius of the transition point is calculated as indicated 97 using equation 3 to produce the density profile 70b as indicated at 98. The transition point 73 is indicated on the density profile 70b in FIG. 7A. It will be appreciated that such a technique could be used for other wood types, or for *p. radiata* taken from areas with different climatic and environmental conditions, by determining a suitable model from experimental data. For example, Douglas Fir has a similar composition to *p. radiata* and therefore a similar density profile model could be assumed whereby the heartwood and sapwood densities are estimated along with the radius of the transition point between the two densities.

Alternatively, and more preferably, the wet density profile could be obtained by measurement. Many ways of assessing the density and particularly the average density of the log or a cant are known including measuring the volume of the material and weighing the material. Many methods are applicable to determining a density profile across a cant and particularly the cut face of a cant. These include profiling using penetrating waves from a microwave source. Other methods may utilise x-rays or particles from a radioactive source.

For example using electromagnetic waves at a number of frequencies in the microwave region it is possible to scan across the cut end of a length of timber and compute a wet density at each point along the diameter. This also provides the location of the heartwood/sapwood transition which is of particular use as this is where the density rises sharply. Methods of extracting water content and dry density of wood using microwave techniques are described in, James W L, You-Hsin Yen, King R J, USDA Forest Products Laboratory Research Note FPL-0250, March 1985 and King R J, Basuel J C, Forest Products Journal, Vol 43(9) 15–22 1993 both of which are incorporated herein by reference. These documents describe using a non-contacting two parameter system (measuring amplitude and phase) operating at a single frequency to extract both water content and dry matter content of wooden materials. The wet density may be found from these values. Alternatively a two frequency system can be used since in the microwave region the dielectric constant of water is frequency dependent while that of the dry matter is not. Conceptually measurement of the dielectric constant of wet timber (which is a linear combination of the water and dry material contributions) at two frequencies allows simultaneous equations to be set up which yield the water content and dry density. Infrared techniques could also be utilised to determine the transition point. Various other techniques for determining density measurements will be known to those skilled in this area of technology. Determining a more detailed density profile through measurement assists in finding a more accurate MoE profile, however it will be appreciated that using a density model such as that described above will also provide a suitable density profile.

FIG. 9C shows the process for calculating an initial MoE profile 62 (in FIG. 6) which can be used a basis for producing refined MoE profiles. The measured acoustic velocity and density profile obtained previously are used to evaluate the initial MoE profile. Firstly a suitable elasticity model is selected as indicated at 99. In selecting a model it is assumed that the density information is measured although it will be appreciated that the information could also be usefully derived from a density model based on knowledge of the wood type. For simplicity it is further assumed that the stem, log or cant is not tapered and is symmetric, although the models could be easily adapted for different geometries. In this case a model is selected in which the $MoE_{max}$ and $MoE_{min}$ are calculated as predicted at 100 corresponding to the sapwood and heartwood elasticities respectively. A parabolic relationship between these two values across the timber is assumed and an appropriate equation formulated from experimental data to represent this relationship. The $MoE_{max}$ and $MoE_{min}$ and the parabolic relationship between the two are determined as follows:

Using equation 2 the discussion earlier lead to the prediction that the high MoE near the bark where the density is near 1050 kg/m³ should be approximately:

$$MoE_{max}=1.05V^2_{meas} \quad\quad 4$$

From experimental data on the 50 log trial the relationship between subsequently measured outer wood elasticity, $MoE_{max}$ and the measured velocity, $V_{meas}$ in fact turned out to be:

$$MoE_{max}=1.0216V^2_{meas}-0.6178\ R^2=0.70 \quad\quad 5$$

The similarity of the expressions, that is small constant and near equality of the slopes, lends confidence to our interpretation of acoustic velocity. The scatter of the data about the regression line (equation 5) is such that the equation predicts the measured values to within 10%.

The core wood density is not as well defined as the outerwood leading to a looser relation between the observed MoE and measured velocity. The trial resulted in the regression:

$$MoE_{min}=0.389V^2_{meas}+2.2559\ R^2=0.41 \quad\quad 6$$

As can be seen this is not quite as close, but still bears some resemblance to the rough prediction:

$$MoE_{min}=0.550V^2_{meas} \quad\quad 7$$

however it still provides a good estimate.

Using the assumption of a parabolic approximation the initial MoE can therefore be defined by:

$$MoE(R)=MoE_{min}+(MoE_{max}-MoE_{min})(R/R_{max})^2$$

where R is the radius and $R_{max}$ is the radius of the stem or log. Once equations have been determined for the model, $MoE_{max}$ and $MoE_{min}$ are calculated as indicated at 100 using equations 5 and 6 and these values are utilised to calculate the initial MoE(R) indicated at 101 using equation 8. It will be appreciated that a maximum value of MoE(R) may be specified, for example 13 GPa as noted before, to avoid unrealistic values being calculated.

Once the initial MoE has been determined an average velocity is calculated 63 as shown in FIG. 9D. At a given radius R the calculated acoustic velocity is determined 102 by:

$$V(R)^2 = \frac{MoE(R)}{Density(R)} \quad\quad 9$$

which follows directly from equation 2. The wet density at each radial point is determined through either a model or measurement as described earlier and the MoE at each radial point is determined from the initial MoE calculated using equation 8. The average, $V_{av}$ of the velocity profile V(R) over the entire radius of the timber is then determined 103. For a cant this is preferably done by integrating the V(R) from the centre of a cant to the maximum radius $R_{max}$ as follows:

$$V_{av} = \frac{1}{R_{max}} \int_0^{R_{max}} V(R)\,dR \quad\quad 10$$

For a stem or log the increasing area of wood at a given speed as the radius increases means that the average velocity is found by:

$$V_{av} = \frac{2}{R_{max}^2} \int_0^{R_{max}} RV(R)\,dR \qquad 11$$

The integration equations assumes a symmetrical stem or log, however this could easily be adapted for non-symmetrical geometries. The average velocity $V_{av}$, is then used in combination with the measured velocity $V_{meas}$, to refine the MoE profile as described previously with reference to FIG. 6.

Figure 10:
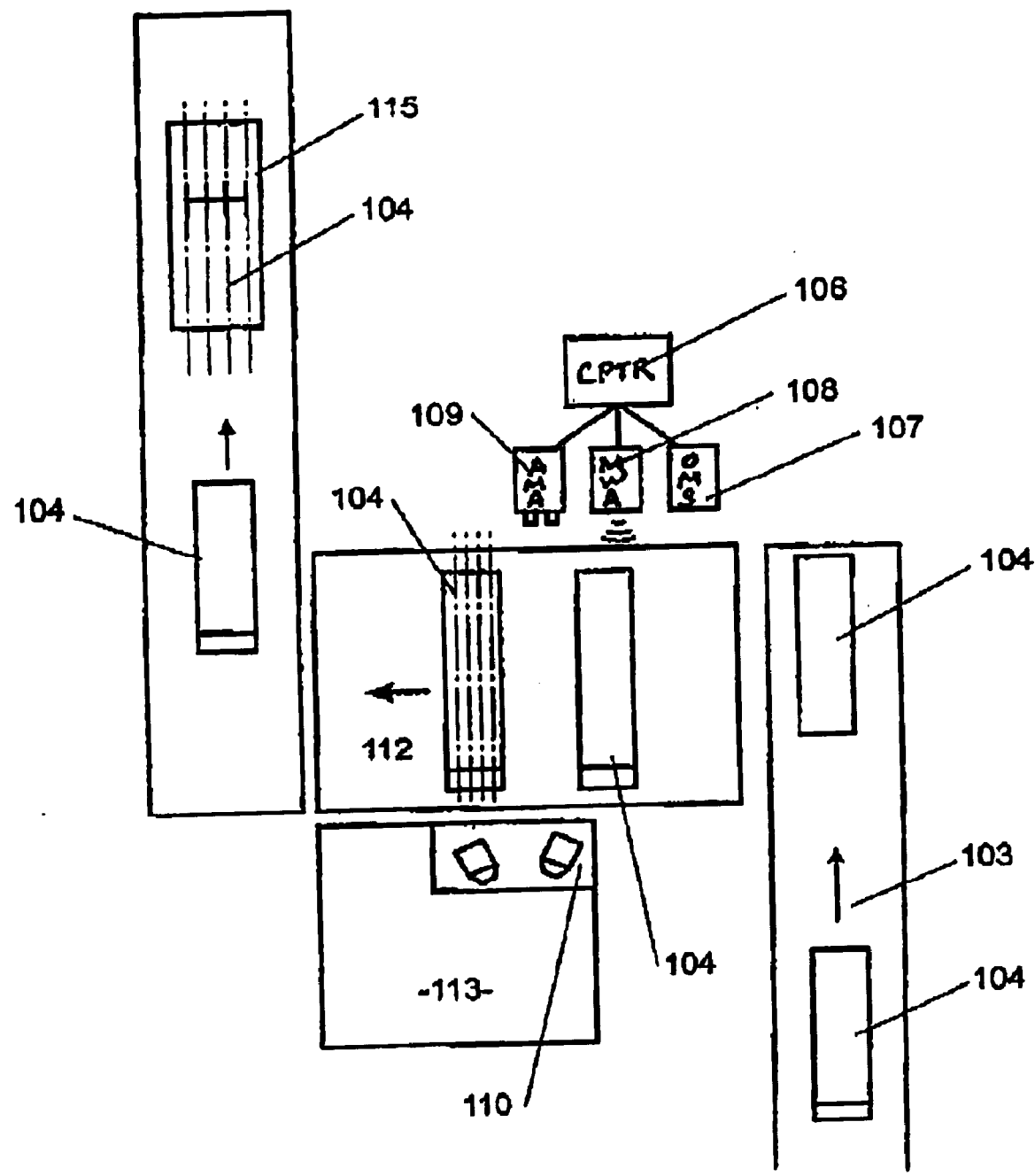

FIG. 10 shows one possible industrial implementation of the method in a saw mill. It will be appreciated that this is illustrative only and not all the apparatus described is necessarily required to implement the method. Further the operation is a cant sawing one but it will be appreciated that the method could be applied to logs, stems or the like. In this timber sawing configuration the apparatus provides an operator with the required information to assist in determining whether the core of the cant or log has a sufficiently high stiffness to be cut for structural timber or whether only the stiff outer wood should be cut. This process involves comparing the MoE profile with a threshold value and finding the radius at which the cant exceeds the threshold. Any part of the cant or log beyond this radius is assumed to be suitable for structural timber and can be cut accordingly.

Logs are processed in a headrig and arrive as cants on a conveyor. Logs or cants are processed in a headrig and arrive as cants or logs 104 on a conveyor belt 103. A cant 104 arriving at an entry point for transfer to an adjustable gangsaw 115 are first unloaded onto a transport system 112 which moves each cant 104 individually in turn into a position in front of an operator station 113. En route to the operator station 113 the cant is inspected by an optical measuring system 107 which measures cant length and width, the latter preferably at several places to give knowledge of cant taper. Preferably a non-contact microwave measuring apparatus 108 measures the wet density and derives a density profile while the cant passes a read head of the measuring apparatus 108. The cant is then conveyed to a position abreast the acoustic measuring apparatus 109 where the velocity of the plane compression wave in the cant via output monitors 110 is measured. Preferably this comprises an accelerometer pressed against the cant 104 end face which detects reverberations within the cant after it is struck by a hammer. The acoustic assembly 109 includes a compressed air driven hammer and an accelerometer on an arm which can extend from the apparatus 109 to contact the cant end face. A typical saw mill environment contains impulsive noise which can interfere with the acoustic signal sought and it is desirable to have a means of raising the cant on vibration isolating lifters above the transport system 112 while the acoustic measurement is made. The measured information is then processed by a computer 106 to provide an operator with MoE information on each successive cant via a monitor 110. The operator postions the subsequent saw cuts for each cant in accordance with MoE information by manipulating laser marker lines 114.

It will be appreciated that the threshold value will be determined according to various parameters such as industry requirements, the margin of error which will be tolerated by the operator and so on. For example an operator may decide that portions of a log or cant with and MoE less than 6 GPa will be suitable for use as industrial timber while portions of the timber with an MoE greater than 6 GPa is suitable for use as structural timber. The radius of the timber at which the MoE exceeds 6 GPa will be the boundary, that is any part of the log less than this radius will be cut for industrial use, while any part of the log outside this radius will be cut for structural use. It will be also appreciated that the operator may instead want to implement a more sophisticated procedure in which the cant is graded in a incremental fashion, rather than using a single threshold value. For example several ranges may be defined where the portions of timber which have MoE values that fall within one of the predefined ranges may be reserved for a specific end use determined for that range. The log or cant could then be cut into the portions in accordance with the determined end uses.

The foregoing describes the invention including preferred forms thereof. Alterations and modifications which will be obvious to those skilled in the art are intended to be incorporated in the scope thereof as defined in the accompanying claims.

What is claimed is:

1. A method of breaking down a stem, log, cant or slab which comprises or includes the steps of:
    determining an acoustic velocity value for the stem, log, cant or slab,
    predicting a stiffness profile across the stem, log, or cant as a function of the acoustic velocity and a density profile across the stem, log, cant or slab, and
    utilising the stiffness profile in cutting the stem, log, cant or slab.

2. A method of estimating elasticity or stiffness across a length of timber including:
    measuring the velocity of a compression wave in the timber,
    providing information as to density for the timber,
    calculating an initial profile of elasticity or stiffness across the timber using an elasticity model of the timber, and
    determining a revised elasticity or stiffness profile using the measured velocity, density information and initial elasticity profile.

3. A method of estimating elasticity or stiffness across a length of timber including:
    measuring the velocity of a compression wave in the timber,
    providing information as to density for the timber.
    calculating a profile of elasticity or stiffness across the timber using an elasticity model of the timber, and
    validating the elasticity or stiffness profile by calculating a velocity of a compression wave in the timber using the density information and elasticity or stiffness profile and comparing the calculated velocity with the measured velocity.

4. A method according to either of claims 2 or 3 wherein providing information as to density for the timber includes providing a profile of density across the timber.

5. A method according to claim 4 including providing the density profile by providing a density profile model of the timber.

6. A method according to claim 5 wherein the density model is based on known characteristics of the wood species.

7. A method according to claim 4 including providing the density profile by measuring a density profile of the length of timber.

8. A method according to claim 6 including measuring a density profile of the length of limber by examining the characteristics of microwaves propagating in the length of timber or a portion thereof.

9. A method according to one of claims 2 or 3 including determining a revised elasticity or stiffness profile by:
  calculating a velocity of a compression wave in the timber using the density profile is and initial elasticity or stiffness profile,
  comparing the measured velocity and the calculated velocity, and
  adjusting the initial elasticity or stiffness profile in accordance with the relationship between the measured and calculated velocities to produce the revised elasticity or stiffness profile.

10. A method according to claim 9 including further improving the elasticity or stiffness profile by:
  recalculating the velocity using the revised elasticity profile,
  comparing the recalculated velocity with the measured velocity, and
  readjusting the revised elasticity profile in accordance with the relationship between the measured and recalculated velocity.

11. A method according to claim 10 including repeating said step of further improving the elasticity or stiffness profile until the elasticity profile produces a calculated velocity which agrees with the measured velocity to within a predetermined accuracy.

12. A method according to claim 10 including measuring the velocity of a compression wave in the timber by:
  inducing a compression wave in the length of timber,
  measuring the fundamental frequency component of the compression wave, and
  determining the velocity using the equation: $V=2 f_0 L$ where V is the velocity of the plane compression wave, $f_0$ is the fundamental frequency and L is substantially length of the timber log.

13. A method according to claim 12 including inducing the compression wave by striking an end of the length of timber.

14. A method according to either claims 2 or 3 wherein the length of timber is a stem, log or cant.

15. A method according to claim 6 wherein the length of timber is a stem, log, or cant and characteristics that the density model is based upon include the density of an outer portion of the stem, log, or cant, the density of an inner portion of the stem, log, or cant, and a transition between the outer and inner densities at a radial position determined by the equation:

$$R_{core} = aD - b$$

where $R_{core}$ is the radius of the transition, D is the diameter of the limber, and a, b are characteristic parameters previously determined for the wood species.

16. A method according to claim 9 including calculating a velocity of the compression wave in the timber calculating a velocity profile of a compression wave in the timber using $$V(R)^2 = \frac{MoE(R)}{Density(R)}$$

where V(R) is the velocity as a function of timber radius, MoE(R) is the modulus of elasticity of the timber as a function of radius and Density(R) is the density of the timber as a function of radius, and averaging V(R) over the timber radius.

17. A method according to claim 16 wherein the length of timber is a cant and V(R) is averaged using;

$$V_{av} = \frac{1}{R_{max}} \int_0^{Rmax} V(R) dR.$$

18. A method according to claim 17 wherein the length of timber is a log and V(R) is integrated using:

$$V_{av} = \frac{2}{R_{max}^2} \int_0^{Rmax} RV(R) dR.$$

19. A method according to any one of claims 1 to 3 including utilizing the estimated stiffness or elasticity profile in determining the placement of sawing points or a sawing pattern for a stem, log, or cant.

20. A method according to any one of claims 1 to 3 including utilizing the estimated elasticity or stiffness profile in sawing side slabs from a stem or log to form a cant or slab.

21. Apparatus for breaking down a tree stem, log, cant or slab of wood including:
  means arranged to determine an acoustic velocity value for the stem, log, cant or slab,
  means arranged to predict a stiffness profile across the stem, log, cant or slab as a function of the acoustic velocity and a density profile across the stem, log, cant or slab.

22. Apparatus for estimating elasticity or stiffness across a length of timber including:
  means for measuring the velocity of a compression wave in the timber,
  means for providing information as to density for the timber, and
  means arranged to calculate an initial profile of elasticity or stiffness across the timber using an elasticity model of the timber, and to determine a revised elasticity or stiffness profile using the measured velocity, density information and initial elasticity profile.

23. Apparatus for estimating elasticity or stiffness across a length of timber including:
  means for measuring the velocity of a compression wave in the timber,
  means for providing information as to density for the timber, and
  means arranged to calculate a profile of elasticity or stiffness across the timber using an elasticity model of the timber, and to validate the elasticity or stiffness profile by calculating a velocity of a compression wave in the timber using the density information and elasticity or stiffness profile and comparing the calculated velocity with the measured velocity.

24. Apparatus according to either one of claims 22 or 23 wherein providing information as to density for the timber involves providing a profile of density across the timber.

25. Apparatus according to claim 24 wherein said means for providing a profile of density across the timber includes a density profile model of the timber.

26. Apparatus according to claim 25 wherein the density model is based on known characteristics of one or more wood species.

27. Apparatus according to claim 4 including means to provide the density profile by measuring a density profile of the length of timber.

28. Apparatus according to claim 26 including means for measuring a density profile of the length of timber by examining the characteristics of microwaves propagating in the length of timber or a portion thereof.

29. Apparatus according to any one of claims 22 or 23 including means arranged to determine a revised elasticity or stiffness profile by:
- calculating a velocity of a compression wave in the timber using the density profile and initial elasticity or stiffness profile,
- comparing the measured velocity and the calculated velocity, and
- adjusting the initial elasticity or stiffness profile in accordance with the relationship between the measured and calculated velocities to produce the revised elasticity or stiffness profile.

30. Apparatus according to claim 29 including means arranged to further improve the elasticity or stiffness profile by:
- recalculating the velocity using the revised elasticity profile,
- comparing the recalculated velocity with the measured velocity, and
- readjusting the revised elasticity profile in accordance with the relationship between the measured and recalculated velocity.

31. Apparatus according to claim 30 wherein said means arranged to further improve the elasticity or stiffness profile is arranged to repeat said steps until the elasticity profile produces a calculated velocity which agrees with the measured velocity to within a predetermined accuracy.

32. Apparatus according to claim 30 wherein said means for measuring the velocity of a compression wave in the timber is arranged to induce a compression wave in the length of timber by striking an end of the length of timber.

33. Apparatus according to any one of claims 21 to 23 also including sawing means arranged to utilise the estimated stiffness or elasticity profile in determining the placement of sawing points or a sawing pattern for a stem, log, or cant.

34. Apparatus according to any one of claims 21 to 23 also including sawing means arranged to utilise the estimated elasticity or stiffness profile in sawing side slabs from a stem or log to form a cant or slab.

35. A method of managing the breakdown of a tree stem which comprises or includes the steps of:
- felling the free stem,
- assessing the free stem for breakdown into sawn timber,
- optionally cutting the tree stem into a log or logs,
- breaking tree stem or log(s) down into a cant and side parts,
- cutting the side puts to structural timber pieces,
- cutting the cant to a mixture of timber pieces cut to structural dimensions and to industrial dimensions, the cutting pattern of the cant having been determined with reliance upon the product of the average density or a density profile across the cant and a function of an average, acoustic speed of the free stem, cant or log.

* * * * *